(12) United States Patent
Tsukioka

(10) Patent No.: US 8,758,705 B2
(45) Date of Patent: Jun. 24, 2014

(54) DISPENSER

(75) Inventor: Hiroyasu Tsukioka, Saitama (JP)

(73) Assignee: Medicatec Kabushiki-Kaisha, Saitama (JP)

( * ) Notice: Subject to any disclaimer, the term of this patent is extended or adjusted under 35 U.S.C. 154(b) by 233 days.

(21) Appl. No.: 13/221,088

(22) Filed: Aug. 30, 2011

(65) Prior Publication Data

US 2012/0255378 A1  Oct. 11, 2012

(30) Foreign Application Priority Data

Apr. 7, 2011 (JP) ................................. 2011-085335

(51) Int. Cl.
*B01L 3/02* (2006.01)
(52) U.S. Cl.
USPC ...... 422/509; 422/510; 73/864.11; 73/864.13; 73/864.16; 73/864.17
(58) Field of Classification Search
USPC .................... 422/509–510, 515, 521–522; 73/864.01–864.25
See application file for complete search history.

(56) References Cited

U.S. PATENT DOCUMENTS

| | | | | |
|---|---|---|---|---|
| 3,815,790 A | * | 6/1974 | Allen et al. | 73/864.13 |
| 4,141,251 A | * | 2/1979 | Oshikubo | 73/864.18 |
| 4,165,646 A | * | 8/1979 | Shapiro | 73/864.13 |
| 4,298,575 A | * | 11/1981 | Berglund | 73/864.13 |
| 4,418,580 A | * | 12/1983 | Satchell et al. | 73/864.13 |
| 4,672,857 A | * | 6/1987 | MacDermott | 73/864.18 |
| 5,192,511 A | * | 3/1993 | Roach | 422/525 |
| 2002/0131903 A1 | * | 9/2002 | Ingenhoven et al. | 422/100 |

FOREIGN PATENT DOCUMENTS

JP  1-46032 B2  10/1989

* cited by examiner

*Primary Examiner* — Jan Ludlow
(74) *Attorney, Agent, or Firm* — Browdy and Neimark, PLLC

(57) ABSTRACT

The dispenser includes a dispensing head extending downward from a cylinder body section with a cylindrical inner space and having a dispensing cylinder with the diameter smaller than that of the inner space of the cylinder body section; a piston capable of being inserted from the inner space of the cylinder body section into the dispensing cylinder section and moving up and down between a dispensing start position located in an upper portion of the dispensing cylinder section and a dispensing end position in a lower portion of the dispensing cylinder section; and a sucking mechanism sucking a liquid from a dripping port at a tip of the dispensing cylinder section up to a position above the dispensing start position inside the inner space of the cylinder body section. The piston is always at the dispensing start position under a liquid surface whenever the dispensing operation is started.

5 Claims, 9 Drawing Sheets

DISPENSER

FIELD

The present invention relates to improvement of a dispenser used at the site of medical treatment for suctioning a sample such as blood or serum and a reagent via operations of a syringe and dispensing the sample or the reagent into each of holes provided in parallel to each other on a titration plate.

BACKGROUND

A dispenser has generally the structure as shown in FIGS. 1A, 1B, 2A and 2B, in which a syringe 2 comprising a cylinder 20 and a piston 21 slidably engaging with the cylinder 20 is assembled to and supported on a bottom side of a dispensing head a (an external contour of which is shown with a chain line in FIGS. 1A-1B, but an internal structure of which is not shown in the figures) supported on a machine body 1 (a portion of which is shown with a chain line, but most portions of which are not shown) and capable of moving in three directions, namely in the right-to-left direction, in the front-to-back direction, and in the vertical direction) in the state where a piston 21 with the cylinder 20 fixed thereto can freely move up and down. When an upper edge side of the piston 21 of the syringe 2 is driven by a stepping motor M provided in a vessel for the dispensing head a and a screw shaft 32 rotates in the regular (forward) direction or in the reverse direction, an operating member 33 and an elevating mechanism 3 move up and down together. When the elevating mechanism 3 is lowered, the piston 21 moves downward as shown in FIGS. 1A and 2A to discharge a sample or a reagent, and when the elevating mechanism 3 is lifted, the piston 21 moves upward to suction the sample or the reagent. Furthermore, a chip b molded separately is dismountably engaged with a nozzle section 20a provided at a lower edge side of the syringe 2 as shown in FIGS. 2A and 2B. With this configuration, when a sample or a reagent is to be suctioned or discharged, the dispensing head a is moved to position the syringe 2 above a vessel c storing a sample, a reagent or the like therein. Then, when the dispensing head a is lowered, a tip of the chip b set on the nozzle section 20a of the syringe 2 is inserted into a liquid stored in the vessel c. In this state, when the elevating mechanism 3 is lifted to lift the piston 21 for the suction operation, the liquid is sucked into the chip b as shown in FIG. 2. After the sample or reagent liquid is sucked into the chip b, the dispensing head a is moved to a position above the vessel, such as a titration plate into which the liquid is to be poured, and the piston 21 is lowered to push out and dispense the liquid which had been sucked into the chip 2 to the vessel.

The prior art-based dispenser as described above has the problem as described below.

In the state where the chip b mounted on the nozzle section 20a of the syringe 2 has been inserted into a sample or a reagent stored in the vessel c as shown in the FIG. 2A, when the stepping motor M operates to drive the elevating mechanism 3 for lifting the piston 21, the liquid, having the volume calculated by multiplying a lifting stroke of the piston 21 by a cross section of the piston 21, is sucked into the chip b. In this sucking operation carried out when the piston 21 is elevated, however, also any air residing in a range from a lower edge portion of the inner space of the cylinder 20 to an inner space of the chip b is sucked together with the liquid of the sample or reagent into a space generated when the piston 21 is elevated, and an air pool is formed between a surface G of the liquid sucked into the chip b and a lower edge portion of the piston 21. Thus, an air layer is generated in the range from the lower edge portion of the piston 21 to the liquid surface G of the liquid having been sucked into the chip b.

The air layer H existing between the lower edge surface of the piston 21 and a surface of the liquid of a sample or a reagent sucked into the chip b functions as a cushion, because the liquid surface G is pressed down via the air layer H when the piston 21 is lowered for dispensing the liquid in the chip b. The cushioning action of the air layer H does not give any negative influence to the dispensing operation, because the air layer H compresses or expands only a little, and movement of the piston 21 is directly delivered to the surface G of the liquid within the chip b and a lowering stroke of the piston 21 accurately defines a volume of the liquid to be dispensed when the piston 21 is lowered for pushing out and dispensing a liquid of a sample or a reagent.

On the other hand, in the dispensing operation with a dispenser, an operation for dispensing a liquid such as a sample or a reagent into each of testing holes provided in an array or arrays on a titration plate is carried successively. Therefore, when a number of samples are to be examined all at once like in, for instance, an inspection facility where a number of samples are gathered, a long time is required for the dispensing work, which disadvantageously lowers the work efficiency.

If a lowering speed of the piston 21 is increased for improving the work efficiency, the air layer is compressed to cause the cushioning effect, and it becomes disadvantageously impossible to decide an accurate dispensing rate corresponding to the lowering stroke. This negative effect becomes more remarkable when a minute quantity of a sample or a reagent is to be dispensed successively and quickly.

PRIOR ART DOCUMENT

Patent Document

Patent document 1: Japanese Patent Publication No. HEI 1-46032

SUMMARY

Problems to be Solved by the Invention

As described above, a liquid of a sample or a reagent is sucked when a piston of a dispenser is lifted, and is dispensed when the piston is lowered. More specifically, when the piston is lifted for sucking the liquid, also air inside a chip is sucked together with the liquid, and an air pool is formed within a sucking cylinder.

When the piston is pushed down, the air pool is turned to an air layer between a tip portion of the piston and a liquid surface and functions as a cushion. During the dispensing operation carried out by slowly lowering the piston, a lowering stroke is accurately reflected to a dispensing rate, so that the cushioning action by the air layer does not cause any negative effect on the dispensing operation. On the other hand, during the dispensing operation, an operation for dispensing a liquid of a sample or a reagent is successively repeated. Therefore, when the dispensing operation is carried out, for instance, at a site such as an inspection facility where a number of samples or the like are gathered, a long time is required for the dispensing operation because of the cushioning action by the air layer, which is not desirable from the view point of work efficiency.

When the lowering speed of the piston is increased to improve the work efficiency, it becomes difficult to obtain an accurate dispensing rate corresponding to the lowering stroke of the piston because of the cushioning action by the air layer, which is disadvantageous. This problem becomes more remarkable, for instance, when a minute quantity of a liquid of a reagent or the like is successively dispensed. Therefore, an object of the present invention is to provide a mechanism to make it possible to improve the efficiency of a dispensing operation as well as to obtain an accurate dispensing rate corresponding to a lowering stroke of a piston.

Means for Solving the Problems

The present invention provides a dispenser as a means for solving the problems as described above, and the dispenser comprises a dispensing head having a dispensing cylinder section extending downwardly from a cylinder body section with a cylindrical inner space formed therein and having a dispensing cylinder section with a diameter smaller than that of the inner space of the cylinder body section; a piston inserted from the inner space of the cylinder body section into the dispensing cylinder and capable of moving up and down in a range from a dispensing start position in an upper portion of the dispensing cylinder to a dispensing end position in a lower portion of the dispensing cylinder; and a suction device for sucking a liquid from a dripping port at a tip of the dispensing cylinder section into an inner space thereof by operating a dispensing operation from a dispensing start position in an upper portion of the dispensing cylinder section and at the same time below a surface of the liquid having been sucked into the inner space of the dispensing cylinder section. Because of the configuration as described above, the dispenser according to the present invention is characterized in that the piston is always at the dispensing start position below a surface of a sucked liquid when a dispensing operation is to be started.

The dispenser according to the present invention is furthermore characterized in that the cylinder body section and the dispensing cylinder section are integrated into an monolithic unit and are dismountably set in a nozzle section at a bottom surface of the dispensing head.

The dispenser is still furthermore characterized in that the piston can provide an intermittent lowering control with a driving device.

The dispenser according to the present invention is still furthermore characterized in that the dispensing head has a cleaning nozzle capable of injecting cleaning water into the inner space of the cylinder body section.

In the prior art, there has been the problem that, during a dispensing operation carried out for sucking and dispensing a liquid of a sample or a reagent by moving up and down a piston for a syringe provided in a dispensing head, when a lowering speed of the piston is increased for improving the work efficiency, it becomes impossible to obtain an accurate dispensing rate corresponding to a lowering stroke of the piston. This problem is caused, because, when the piston is lifted for sucking a liquid of a sample or a reagent, the air sucked together with the liquid resides within a space between a lower edge surface of the piston and a surface of a sucked liquid to form an air layer, and the air layer acts as a cushion. Therefore, this problem can be solved by providing a structure of a dispenser in which an air layer is not formed between a lower edge surface of a piston and a liquid surface while the piston is being lifted or lowered. The present inventor thought of the idea for solving the problem by providing a dispenser having the configuration in which the elevating operations of a piston are carried out in the state where a piston (sealing section) provided at a tip of a piston rod does not contact air and a liquid directly contacts a bottom surface and a top surface of the piston, namely in the state where a piston is always kept in a liquid while the elevating operations are carried out. The present invention was made based on the idea.

Effects of the Invention

In the dispenser according to the present invention, a piston is engaged and set in a dispensing cylinder and moves up and down between a dispensing start position set at an upper edge portion of the dispensing cylinder and a dispensing end position set at a bottom end portion of the dispensing cylinder for sucking and dispensing a liquid of a sample or a reagent. Namely, the piston is always kept in a liquid during the elevating operations and is not affected by a cushioning action of an air layer residing in the dispensing cylinder. Because of the configuration of the dispenser according to the present invention, it is possible to dispense a liquid of a sample, a reagent, or the like at an accurate dispensing rate corresponding to a lowering stroke of the piston regardless of whether the piston is lowered slowly or quickly.

BRIEF DESCRIPTION OF THE DRAWINGS

FIG. 6A is a developed longitudinal front view illustrating the state where a sealing section at a tip of the piston is pulled up above a dispensing start position and is positioned within a cylinder body with a liquid sucked into the cylinder body; FIG. 6B is a longitudinal front view illustrating the state where the piston has been lowered from the position shown in FIG. 6A to sink the sealing section of the piston into the liquid and set at the dispensing start position; and FIG. 6C is a longitudinal front view showing the state where the piston has been lowered from the position shown in FIG. 6B to a dispensing end position at an end of the lowering stroke of the piston;

DETAILED DESCRIPTION

A dispenser according to the present invention is described in detail below with reference to the drawings.

Embodiment 1

Figure 3:
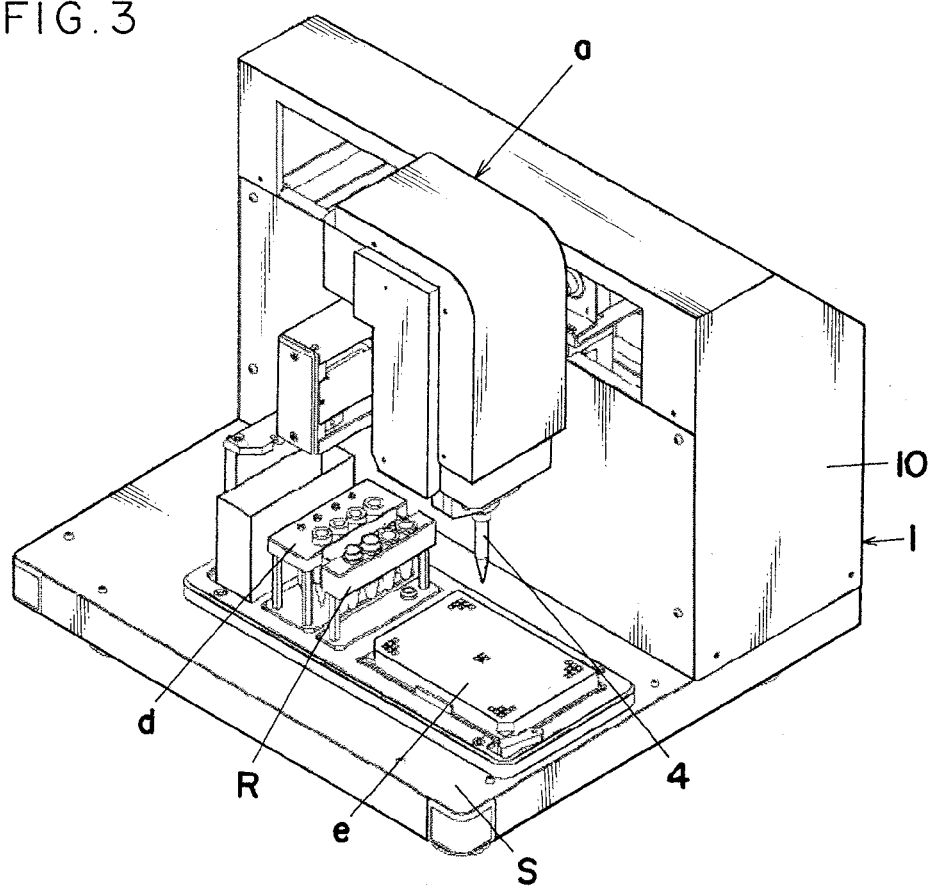
FIG. 3 is a perspective view showing a dispenser according to one embodiment of the present invention.

In FIG. 3, reference numeral 1 is a machine body (dispenser). A machine housing 10 is installed in the latter half side of the machine body 1, a dispensing head a is connected to the front side of the machine housing 10, and a dispensing syringe 4 is assembled on a bottom portion of the dispensing head a. Furthermore, a station S is provided on a top surface of the machine body 1 and in the front of the machine housing 10. A chip rack R supports chips (each of which corresponds to the dispensing syringe 4 in this case) provided in parallel to each other thereon on the station S. A rack d supporting vessels c for a sample or a reagent positioned in parallel to each other is provided on the chip rack S on the station. A titration plate e with testing holes is provided in alignment on the station. The dispensing head a can be moved by an operating mechanism (not shown) provided in front of the machine housing 10 in three directions, namely the horizontal direction X, in the vertical direction Z, and in the front-to-back direction Y.

Figure 4:
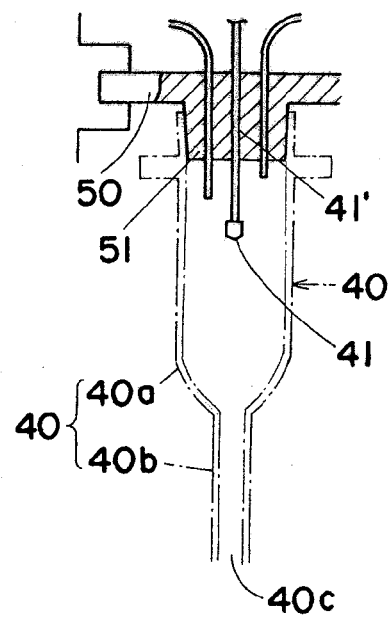
FIG. 4 is a partially broken front view showing a dispensing syringe assembly section in the embodiment.

The dispensing syringe 4 assembled onto a bottom portion of the dispensing head a has a structure according to one embodiment as shown in FIG. 4. Namely the dispensing syringe 4 comprises a cylinder 40 having a cylindrical inner space, a funnel-formed large-diameter cylinder body section 40a provided at the lower edge side of the cylinder 40 and tapered downwardly, and a dispensing cylinder section 40b provided at the lower end portion of the cylinder body section 40a with an inner cylindrical space smaller than that of the cylinder body section 40a and also having a dripping port 40c at the lower edge portion thereof. Downwardly and lower here are used to describe the direction toward the opening of the syringe through which the sample is suctioned.

The large-diameter cylinder body section 40a and a small-diameter dispensing cylinder 40b are molded into a monolithic body to form the cylinder 40. The cylinder 40 is assembled in the dispensing head a by engaging an open port at the upper edge portion of the cylinder body section 40a around the nipple-formed cylindrical portion 51 provided on a bottom surface of an assembly block 50 provided on a bottom surface of the dispensing head a as shown in FIG. 4. In this example, the cylinder 40 is removably engaged around the cylindrical assembly portion 51, and because of this structure, a number of chips can be provided in parallel to each other on a chip rack R on a station S so that the chips can easily be set on or off from the chip rack R as necessary.

Figure 5:
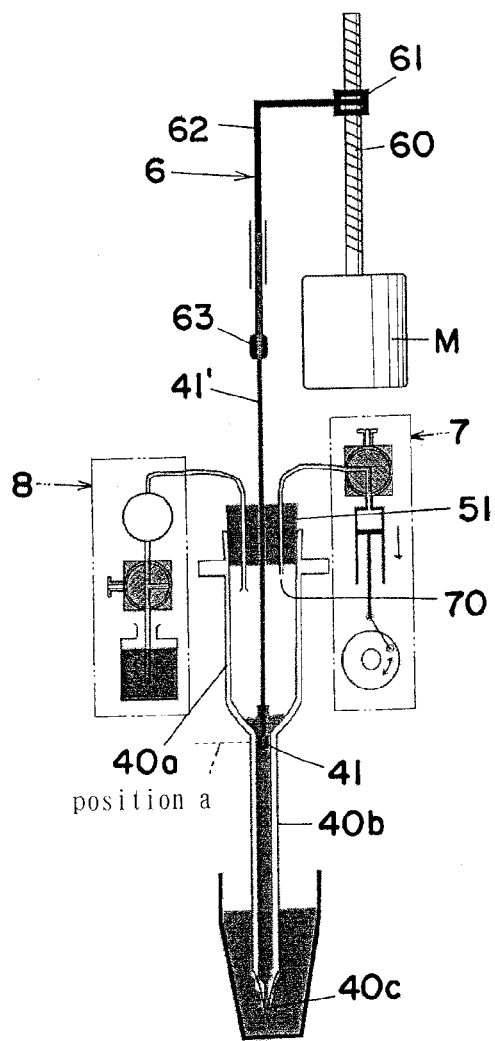
FIG. 5 is a developed longitudinal front view illustrating a dispensing mechanism section in the embodiment.

A piston 41 slidably inserted into this cylinder 40 is attached to a tip portion of a rod-shaped piston rod 41', and is inserted from an open port provided at an upper edge portion of the cylinder body section 40a. In that sense, a structure and a form of the piston may be like that of an ordinary cylinder. In this example, however, as shown in FIG. 5, the piston rod 41' has a smaller diameter than a bore of an inner space of the dispensing cylinder section 40b and is set on a lower edge thereof. In addition, the piston rod 41' is molded into a sealing section with a resin material or an elastic material, so that the piston rod 41' can be engaged in a cylindrical inner space of the dispensing cylinder section 40b having a small diameter in the water-tight state.

When a piston 41 provided at a lower end portion of the piston rod 41' is engaged in an inner space of the small-diameter dispensing cylinder 40b in the water-tight state, a liquid of a sample or a reagent is sucked or discharged.

An upper edge side of the piston rod 41' linked to the piston 41 is inserted into an inside space of the dispensing head a surrounded with a cover through a through-hole provided at a central portion of the cylindrical assembly section 51 provided on a bottom surface of the dispensing head a as well as through a through-hole provided on the assembly block 50 and is connected to the elevating mechanism 6. When the elevating mechanism 6 moves up and down, the piston rod 41' moves up and down correspondingly to move the piston 41 upward or downward correspondingly.

The elevating mechanism 6 according to this embodiment comprises, as shown in FIG. 5, a stepping motor M assembled to and hoisted from an assembly housing (not shown) on a vessel for the dispensing head a, an operating member 61 screwed around a screw shaft 60 extending in the vertical direction and driven and rotated when the motor M rotates, an operating rod 62 connected to the operating member 61, and a joint 63 for connection between a lower end portion of the operating rod 62 and an upper end portion of the piston rod 41'. When the stepping motor M turns in the regular (forward) direction or in the reverse direction, the screw shaft 60 rotates in the regular (forward) direction or the reverse direction, respectively, to cause upward movement or downward movement of the operating member 61 engaged around the shaft 60, thus the piston 41 is moved up or down by rotation of the motor M.

The stepping motor M controls elevating operations of the piston 41 by the elevating mechanism 6, and control by the stepping motor M can be switched to permit operations for sucking and dispensing a liquid of a sample or reagent by moving up and down the piston 41 in the state where the piston is always kept in a liquid. In other words, control by the stepping motor M is provided so that the piston 41 goes out of the dispensing cylinder section 40b to the upward position shown in FIG. 6A and is located at position C in FIG. 6A exposed to an inner space of the cylinder body section 40a to release sealing for the dispensing cylinder section 40b before the dispensing operation is started.

Elevating operations of the piston 41 are carried out in association with operations of the elevating mechanism 6 under controls by the stepping motor M. Controls by the stepping motor M are provided so that the lowering stroke ends at the position (position b shown in FIG. 6C) corresponding to the timing when the piston 41 reaches a lower edge portion of the inner space of the dispensing cylinder section 40b and finishes dispensing a sucked liquid, and also so that the rising stroke ends at the position (position a shown in FIG. 6B) when the piston 41 finishes sucking a liquid into the inner space of the dispensing cylinder 40b and reaches the dispensing start position. Therefore, when the stepping motor M runs to drive the elevating mechanism 6, the piston 41 moves up and down between the position a and the position b, so that a liquid is sucked into the dispensing cylinder section 40b and then dispensed by a volume decided by the stroke of the piston 41.

When the piston 41 is pulled up, goes out of the dispensing cylinder section 40b, and is positioned inside the cylinder body section 40a, sealing for the inner space of the dispensing cylinder section 40b by the piston 41 is released. In this state, a sucking mechanism 7 (described later) having a suction port 70 communicated to the cylinder body section 40a is operated to suck air into the cylinder body section 40a, a liquid is sucked up from a cylinder tip of the dispensing cylinder section 40b having been dipped into the liquid, and the liquid flows into the cylinder body section 40a. In this state, when a sucking operation of the sucking mechanism 7 is stopped and the inside space of the cylinder body section 40a is sealed tightly, a surface of the sucked liquid is kept at a constant level in the cylinder body section 40a above the dispensing cylinder section 40b. In the state where the liquid surface is kept at a constant level, when the piston 41 is lowered to the position a which is the dispensing start position, the piston 41 is dipped into the liquid with the lower edge surface and the top surface directed contacted to the liquid, so that there is no air layer between the lower edge surface and the liquid. In this state, when the piston 41 having been dipped into the liquid is lowered to the lower stroke end position corresponding to the position b, the liquid, having an accurate volume defined by the stroke from the position a to the position b within the dispensing cylinder section 40b, is discharged and dispensed from the dripping port 40c at a tip of the dispensing cylinder section 40b, because there is no air layer under the bottom surface of the piston 41.

When the dispensing operation is finished, the liquid residing inside the cylinder body section 40a up to a position above the top surface of the piston 41 follows the lowering movement of the piston 41 and flows into the dispensing cylinder section 40b. The residing liquid is still present on the top surface of the piston 41 which has reached to the lowering stroke end position which is also the dispensing end position, so that the piston 41 is kept in the liquid of a sample or a reagent to be sucked and dispensed.

Because of the configuration as described above, when the piston 41 is moved upwardly by the stroke from the lowering stroke end position (position b) up to the dispensing start position (position a) for sucking the liquid, the liquid is sucked in the state where the bottom surface of the piston 41 is always in direct contact with the liquid and because there is no air layer under the bottom surface of the piston 41, the liquid is sucked into the dispensing cylinder by the volume accurately caused by the stroke of the piston 41.

Because the sucking and dispending operations by the piston 41 are carried out in the state where the piston 41 is always kept immersed in the liquid, even if the elevating speed of the piston 41 is increased, the liquid is always dispensed in an accurate volume, because there is no air layer under the bottom surface of the piston 41.

Figure 7:
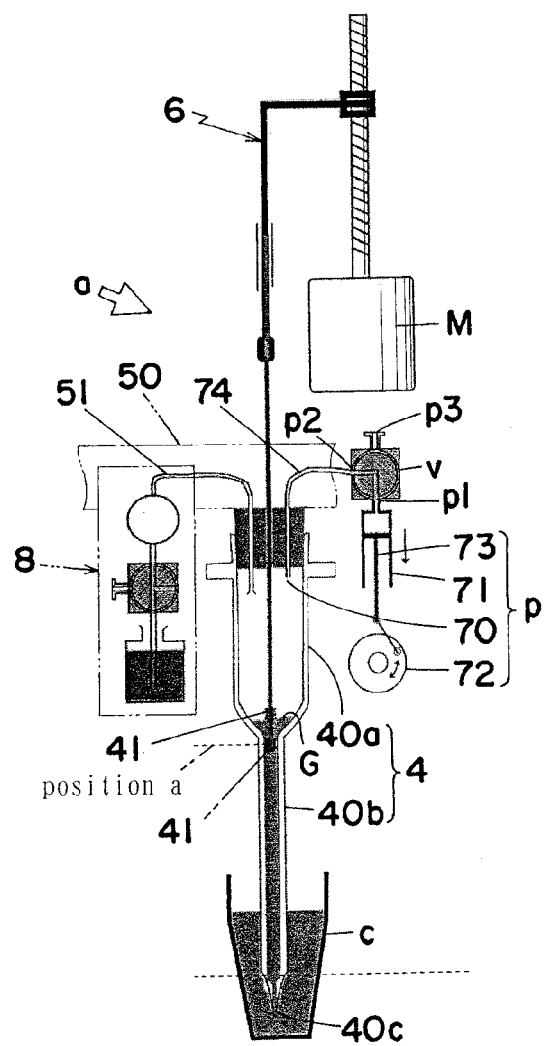
FIG. 7 is a longitudinal front view illustrating a state the piston of the dispensing mechanism has been moved upwardly above the dispensing start position and the liquid in a vessel has been sucked into the cylinder body by a sucking device.

In the dispenser according to the present invention, the piston 41 must always be kept immersed in a liquid of a sample or a reagent whenever the dispensing operation is started. To satisfy this requirement, the sucking mechanism 7 with the suction port 70 communicated to the inner space of the cylinder body section 40a is required, in the state where the piston 41 is pulled off from the dispensing cylinder section 40b and is positioned in the cylinder body section 40a, to suck a liquid of a sample or a reagent from the dripping port 40c at the tip of the dispensing cylinder section 40b up by causing a sucking pressure to build up inside of the cylinder body section 40a so that the liquid surface is above the top surface of the piston 41 in the cylinder body section 40a. As long as this requirement is satisfied, configuration of the dispenser according to the present invention is not limited to that described above. In this embodiment, as shown in FIG. 7, a suction pump p comprises a sucking cylinder 71 assembled to a mounting housing (not shown) provided in a dispensing head a and a piston 73 capable of reciprocally moving in response to rotations of a crank wheel 72 to go into or come out from the sucking cylinder 71. A suction port of the suction pump p is connected to a port p1 of a switching valve v having a port p2 and a port p3 in addition to the port p1. Furthermore, a suction pipe 74 is connected to the port p2 of the switching valve v, and a tip side of the suction pipe 74 is inserted, through a through-hole in the cylindrical assembly section 51 provided on a bottom surface of the assembly block 50 in the housing for the dispensing head a. The suction port 70 is opened in the cylinder body section 40a.

Figure 6C:
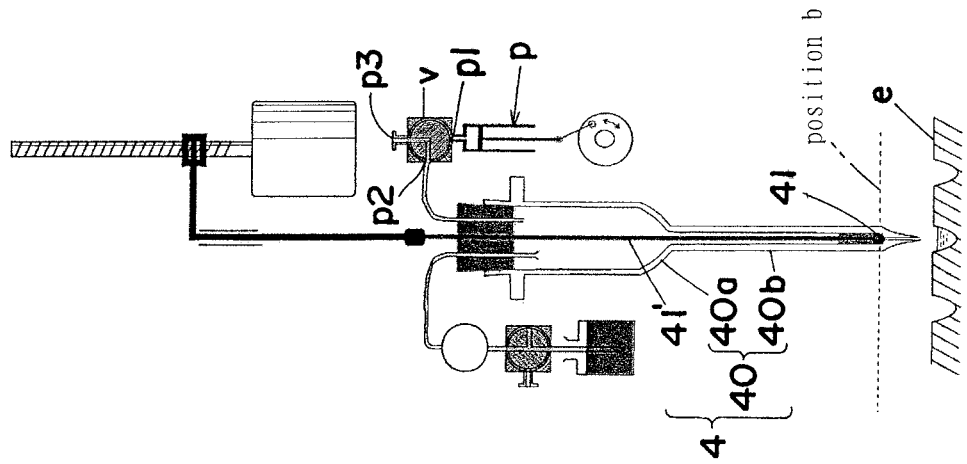
FIGS. 6A, 6B, and 6C are views illustrating an elevating operation of a piston in the dispensing mechanism section, where
Figure 6B:
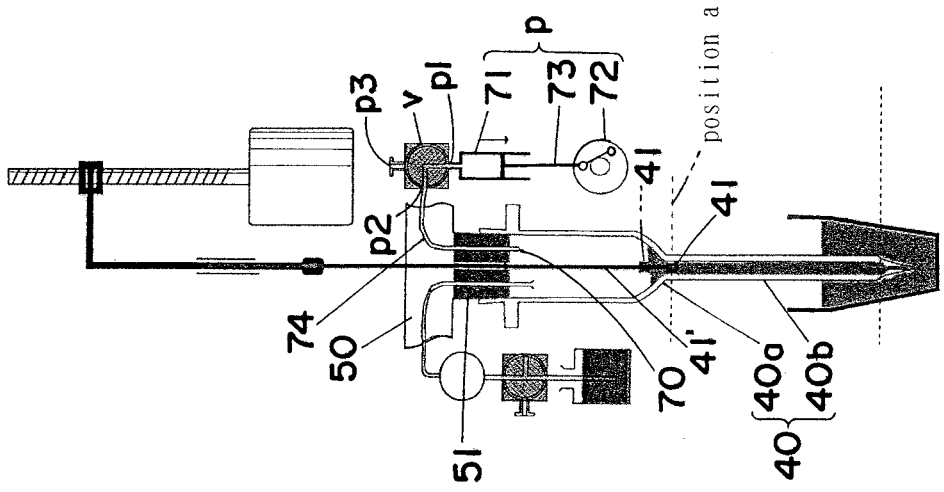
Figure 6A:
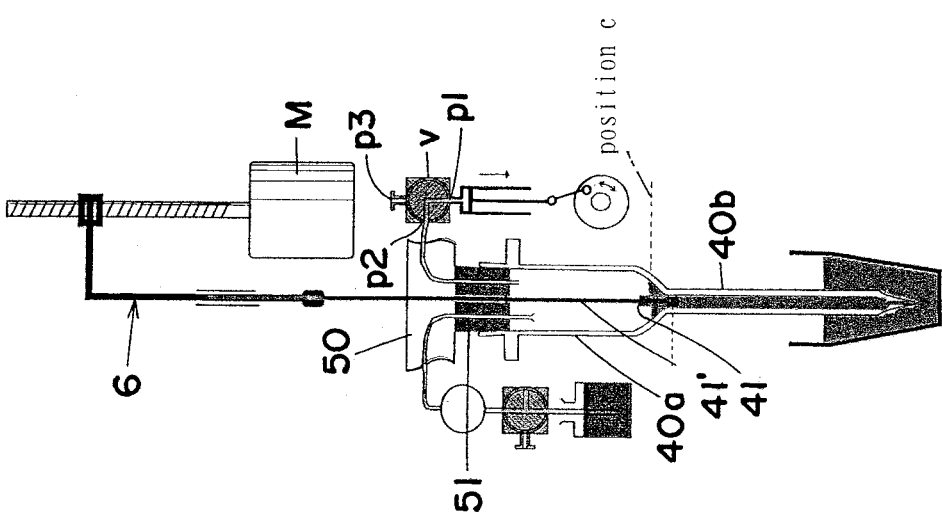
Figure 8:
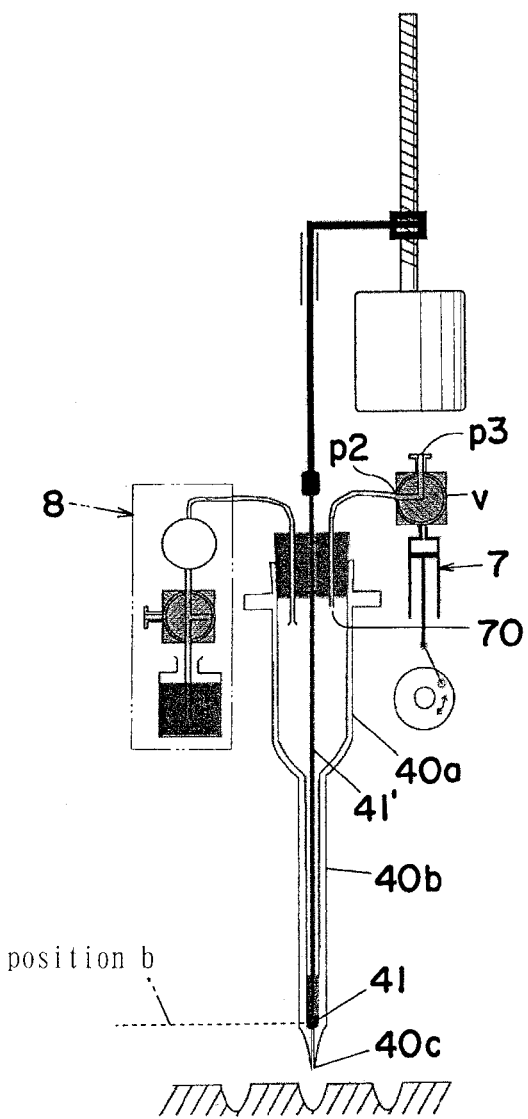
FIG. 8 is a longitudinal front view illustrating the state of the piston when the dispensing mechanism section is lowered.

Because of the configuration as described above, in the state where the piston 41 for the syringe 4 has been pulled up into the cylinder body section 40a as shown in FIG. 6A, when the switching valve v is switched to the state where the port p1 and the port p2 are communicated to the pump p and the cylinder body section 40a respectively as shown in FIG. 6B, the sucking operation of the pump p is started. Then, air is sucked by a volume corresponding to a stroke of the piston 73 from inside of the cylinder body section 40a, and a liquid is sucked up by a volume corresponding to the air volume into the cylinder body section 40a. With this operation, the liquid is sucked up to a position above the dispensing cylinder section 40b as shown in FIG. 7. A surface G of the sucked liquid is above the dispensing start position a for the piston 41.

In the state described above, when an operation of the pump p is stopped to keep an air pressure within the cylinder body section 40a at a constant level and then the piston 41 is lowered to the dispensing start position (corresponding to the position a) as shown in FIG. 6B, the piston 41 is immersed in the liquid. Then, the switching valve v of the pump p is switched to the state where the port p2 is connected to the port 3 for releasing air to the outside. In this state, when the piston P is driven to start a lowering operation and the piston 41 is lowered to the dispensing end position (corresponding to the position b), the liquid is pushed out by the volume corresponding to the stroke of the piston 41 from the position a to the position b from the dripping port c at a lower end of the dispensing cylinder 40b and is dispensed into the test holes provided at a titration plate c provided as shown in FIG. 6C. At the same time, air flows into the cylinder body section 40a by a volume equal to the volume of the discharged and dispensed liquid from the port p3 for releasing air of the switching valve v. Thus, a volume of a liquid is always accurately kept at a constant level.

This sucking mechanism 7 is provided for the purpose to suck a liquid into the cylinder body section 40a so that the sealing section 41a is immersed in the liquid without fail when starting the dispensing operation. For carrying out the dispensing operation, the piston 41 is pulled upward as shown in FIG. 6A to suck up the liquid into the cylinder body section 40a, and then the piston 41 is lowered to the dispensing start position (corresponding to the position a) as shown in FIG. 6B to immerse the piston 41 in the liquid. Then the piston 41 is moved up and down between the dispensing start position (a) and the dispensing end position (b). Therefore, it is not necessary to run the sucking mechanism 7 while the sucking and dispensing operations are being carried out. During the sucking and dispensing operations, the port p3 for releasing air of the switching valve v is communicated to the inner space of the cylinder body section 40a as shown in FIG. 6C.

The device 8 surrounded by a chain line in FIG. 5 through FIG. 9 is a cleaning water injection mechanism. This cleaning water injection mechanism is assembled connected to the dispensing head a and is used to clean the inside of the dispensing syringe 4 when the operation for sucking and dispensing a sample, a reagent, or the like is finished, because the operation is carried out by the dispensing syringe 4 mounted on the cylindrical assembly section 51 provided on a bottom surface of the assembly block 50 assembled to the dispensing head a.

This cleaning water injection mechanism 8 is described in further detail below with reference to the configuration shown in FIG. 9. The cleaning water injection mechanism 8 comprises an air-liquid pump sp for sucking air or a liquid from a suction port and discharging from a discharge port when driven by a motor (not shown), a cleaning water tank t connected via the switching valve v to the suction port of the air-liquid pump sp, and a connection pipe 80 connected to the discharge port of the air-liquid pump sp for guiding cleaning water sucked up by the air-liquid pump sp to inside of the dispensing syringe 4 connected to the cylindrical assembly section 51 provided on a bottom surface of the assembly block 50 (not shown) connected to the dispensing head a. A tip of the connection pipe 80 is inserted through a through hole provided on the assembly block 50 as well as through a through hole provided in the cylindrical assembly section 51 into the cylinder body section 40a of the dispensing syringe 4 assembled to the cylindrical assembly section 51, and a nozzle 81 is attached to the tip portion. The switching valve v has a port p4 for connection to a suction port of the air-liquid pump sp, a port p5 for releasing air to the outside, and a port p6 for connection to the cleaning water tank t filled with the cleaning water. Therefore, the switching valve v can operate in two operating modes of: 1) communicating the suction port of the air-liquid pump sp to the cleaning water tank t; and 2) releasing air to the outside.

Figure 9:
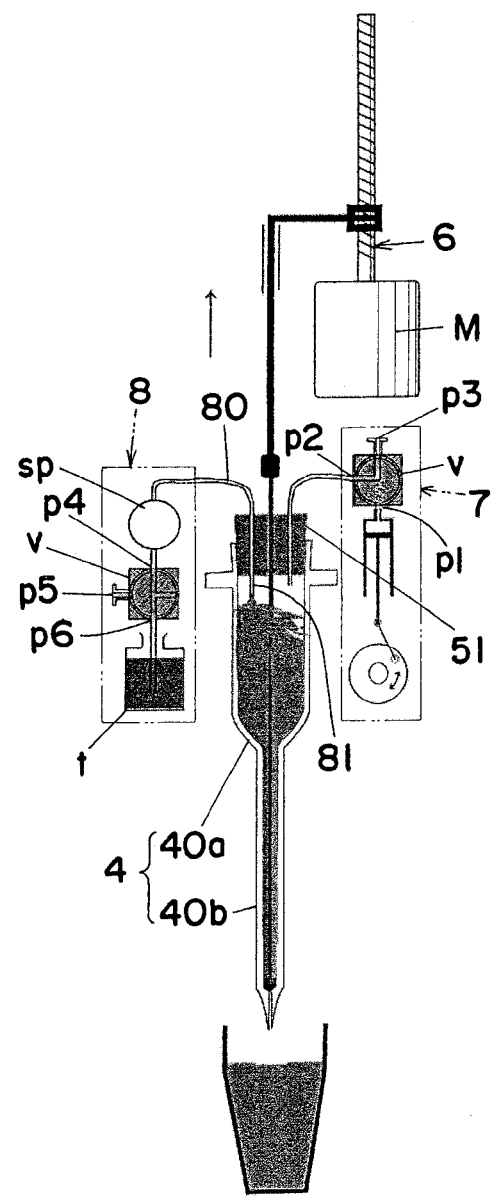
FIG. 9 is a longitudinal front view illustrating the state where a cleaning water injecting mechanism of the dispensing mechanism section is operated to inject the cleaning water into a cylinder of the dispensing syringe.

The cleaning water injection mechanism 8 and the sucking mechanism 7 are assembled at symmetrical positions to the dispensing head a as shown in FIG. 9.

The work for cleaning inside of the dispensing syringe 4 by the cleaning water injection means 8 is carried out through the following steps.

At first, the switching valve v is switched so that the suction port of the air-liquid pump sp is connected to the cleaning water tank t. Then, the air-liquid pump sp is run to inject the cleaning water sucked up from the cleaning water tank t to the inside of the cylinder body section 40a of the syringe 4 for cleaning. In this step, the elevating mechanism 6 is run to lower the piston 41 of the dispensing syringe 4 to an end position of a lowering stroke of the piston 41, namely the dispensing end position (corresponding to the position b) so that the inner space of the dispensing cylinder 40b is filled with the cleaning water. If an exhaust port (not shown) is provided in the dispensing syringe 4, the exhaust port is opened to accelerate pouring of the cleaning water into the dispensing syringe 4. If the sucking mechanism 7 described above is assembled, the switching valve v of the sucking mechanism 7 is set in the state where the port 3 and the port 2 are communicated to the inner space of the dispensing syringe 4 so that the port p3 and the port p2 are communicated to the inner space of the dispensing syringe 4 so that air inside the dispensing syringe 4 is exhausted via the port p3 of the sucking mechanism 7 to the atmosphere.

When the cleaning water is filled in the dispensing syringe 4 by a specified volume, operation of the air-liquid pump sp is stopped and the exhaust port provided in the dispensing syringe 4 is closed. Alternatively, the port 3 of the switching valve v is closed to shut down the communication between the inner space of the dispensing syringe 4 to the atmospheric air for preserving the poured cleaning water inside the dispensing syringe 4. In this state, a cleaning operation for inside of the dispensing syringe 4 is carried out by running the elevating mechanism to move up and down the piston 41 in repetition.

Figure 10:
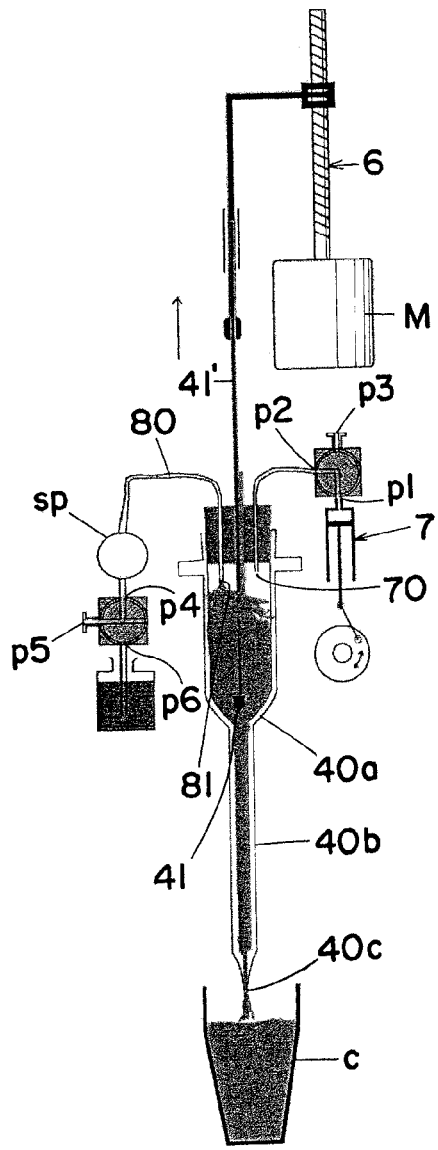
FIG. 10 is a longitudinal front view illustrating the state where the cleaning water injecting mechanism of the dispensing mechanism section is operated to inject air into the cylinder of the dispensing syringe for discharging the cleaning water inside the cylinder from a dripping port to the outside.

When the cleaning operation by moving up and down the piston 41 is finished, the exhaust port of the port p3 of the switching valve v of the sucking mechanism 7 is kept closed, and the piston 41 is pulled up into inside of the cylinder body section 40a, and the valve b of the cleaning water injection mechanism 8 is switched so that the suction port of the air-liquid pump sp is communicated via the port 5 to the atmospheric air as shown in FIG. 10. In this state, the air-liquid pump sp is run to inject the air sucked with great force through the port p5 to inside of the cylinder body section 40a of the dispensing syringe 4 from a nozzle 81. Because of the injection pressure, the cleaning water inside the dispensing syringe 4 is discharged from the dripping port 40c at a tip of the dispensing cylinder section 40b, thus the cleaning work being finished.

With the dispenser having the cleaning water injection mechanism 8, it is possible to clean the dispensing syringe 4 set under the dispensing head a with cleaning water and thus to prevent contamination of the dispensing syringe 4 without the need of replacing the dispensing syringe 4 each time the dispensing operation is carried out.

Embodiment 2

FIG. 11 through FIG. 18 each show a dispenser according to another embodiment of the present invention. The dispenser according to this embodiment (embodiment 2) is basically the same as that described in Embodiment 1. However, the disperser according to Embodiment 2 is different from that described in Embodiment 1 in the following respects. In the dispenser according to Embodiment 1, only one syringe 4 is assembled to a bottom portion of the dispensing head a, while a plurality of syringes 4 can be assembled in parallel to each other and therefore the dispenser according to Embodiment 2 has a holding member for holding the plurality of syringes 4. In addition, in the dispensing syringe 4 of the dispenser according to Embodiment 2, the dripping port 40c at a tip of the small-diameter dispensing cylinder 40b, which is provided under and connected to the cylinder body section 40a, has the same aperture equal to the inner diameter of the dispensing cylinder 40b.

Figure 11:
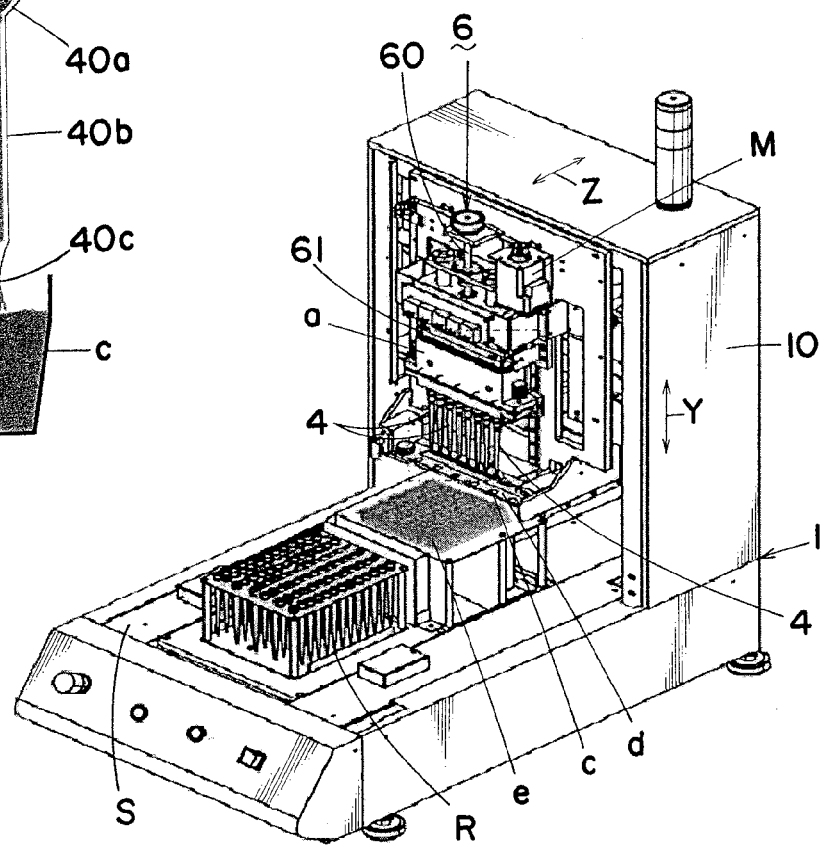
FIG. 11 is a general perspective view illustrating a dispenser according to another embodiment of the present invention.

The dispenser according to Embodiment 2 is described more specifically with reference to the related drawings. FIG. 11 is a perspective view showing the dispenser. FIG. 11 shows a dispenser 1 (machine) as a whole, a machine housing 10 provided in the upright state at a rear portion of a top surface of the dispenser 1, a dispensing head a provided in the hoisted state in the front portion of the housing 10, a dispensing syringe 4 assembled to a bottom portion of the dispensing head a, a station S provided in a front-half side of the top surface of the machine 1, a rack d provided under the dispensing head a and holding vessels (bottles) c provided in parallel to each other and each containing a liquid of a sample, a reagent, or the like, a titration plate e provided on the station S in the front of the rack d, and a chip rack R provided on the station S in front of the titration plate e and along the front edge of the top surface of the station S.

The dispensing head a is movably provided in the front of the housing 10 so that sucking and dispensing operations for a liquid of a sample or a reagent can be carried out by the dispensing syringe 4 provided on the bottom portion of the dispensing head a. In this example, the rack d holding vessels (bottles) c with a liquid of sample or the like filled therein, the titration plate e, and the chip rack R are aligned in the front-to-rear direction in front of the dispensing head a. Therefore, the dispensing head a can move in two directions, namely the vertical direction (in the Y-axial direction) and the front-to rear direction (in the Z-axial direction).

The dispensing head a has an elevating mechanism 6 for moving the piston rod 41' of the dispensing syringe 4 up and down as in Embodiment 1, although a portion thereof is not shown in the figure. When the stepping motor M turns in the regular (forward) direction or in the reverse direction, the operating member 61 screwed around the screw shaft 60 moves upward or downward to move the piston rod 41' connected to the piston 41 upward or downward.

However, the elevating mechanism 6 in Embodiment 2 is different from that in Embodiment 1 in the route for delivering a rotating force from the output shaft of the stepping motor M to the screw shaft 60 as well as in the linkage means between the operating member 61 and the piston 41.

Figure 1:
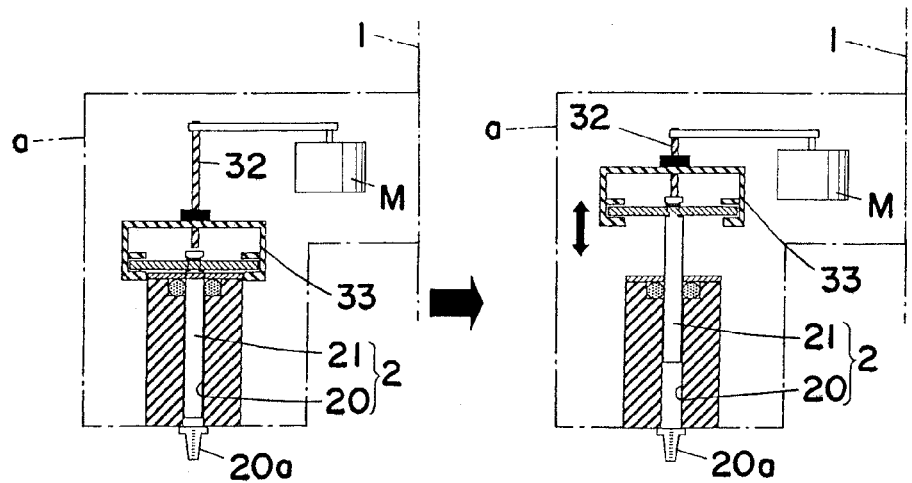
FIG. 1 is a conceptual view illustrating a dispensing syringe section of a dispenser based on the prior art.
Figure 2:
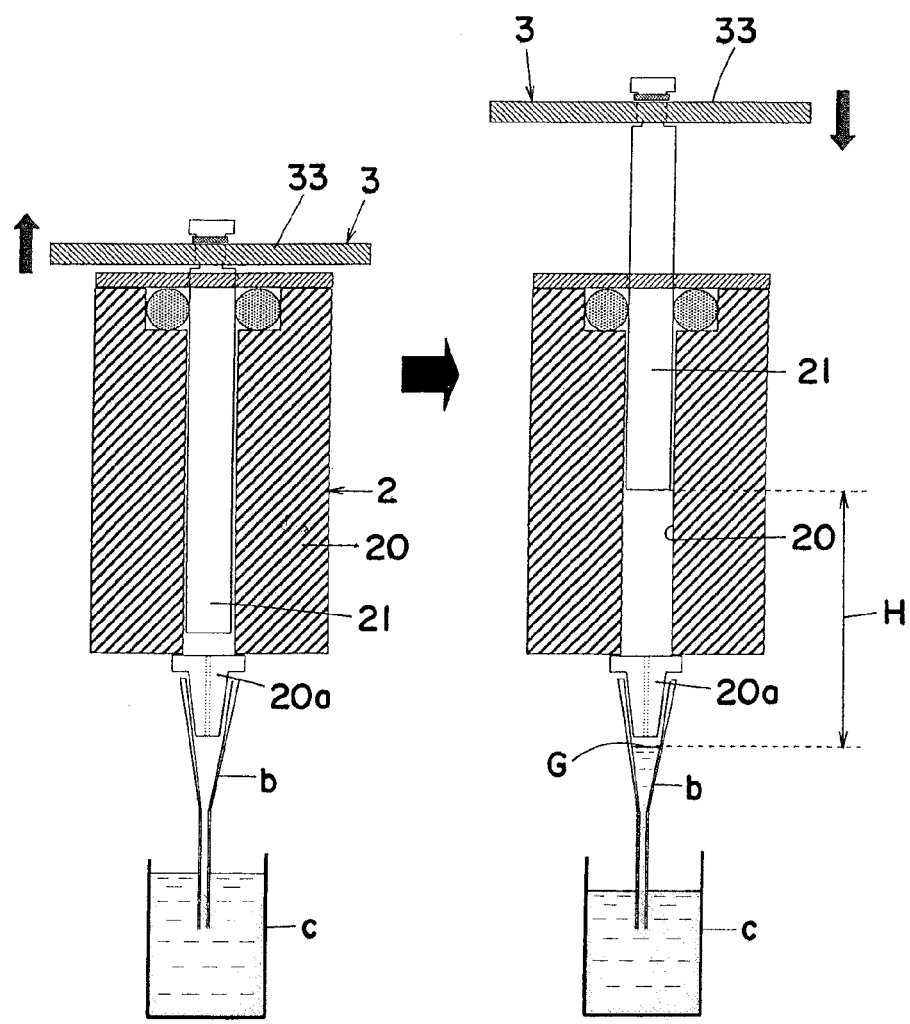
FIG. 2 is a view illustrating a sucking operation of the dispensing syringe section shown in FIG. 1.
Figure 12:
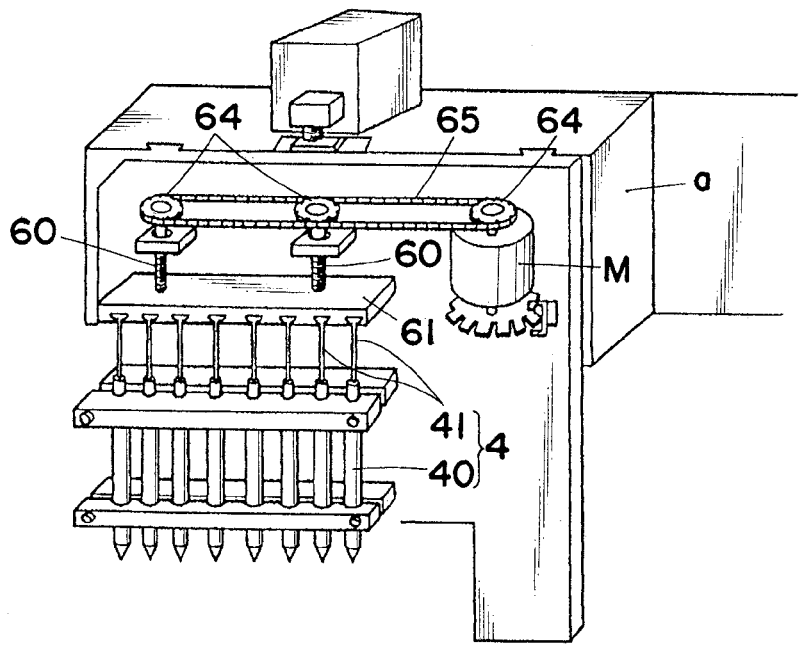
FIG. 12 is a view illustrating a elevating mechanism of the dispenser shown in FIG. 11.
Figure 12:
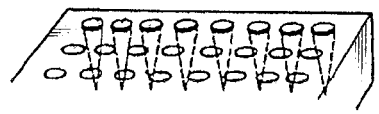

In the disperser according to Embodiment 1, the output shaft of the stepping motor M, which is connected in the directly conductive state to a lower edge of the screw shaft 60 and the operating member 61 screwed around the screw shaft 60 and capable of moving up and down, is directly linked to the piston rod 41' of the piston 41 via the operating rod 62. In Embodiment 2, however, the elevating mechanism 6 is the same as that employed in the dispenser disclosed in Japanese patent Publication No. HEI 1-46032 previously filed also by the present inventor, incorporated by reference herein in its entirety. Namely, as shown in FIG. 12 which is equivalent to FIG. 2 in the patent publication above, a sprocket 64 is assembled to the output shaft of the stepping motor M, and a conduction chain spanned over the sprocket 64 is also spanned over the sprockets 64 assembled to the top edge sides of the screw shafts provided in parallel to each other, so that the rotating force of the output shaft of the stepping motor M is conducted to the screw shafts 60 via the conduction chain 60. Furthermore, the operating member 61 has a horizontally long and flat form and is screwed to the lower edge side of the screw shaft 60. The upper edge portions of the pistons 41 of the syringes 4 assembled in the aligned state to the bottom surface of the dispensing head a are linked to the flat-formed operating member 61, so that the pistons 41 of the syringes 4 can be moved up and down simultaneously.

The sucking mechanism 7 and the cleaning water injection mechanism 8 are assembled in the dispensing head a according to Embodiment 2 like in the dispensing head a according to Embodiment 1.

The dispensing syringe 4 assembled to a bottom portion of the dispensing head a has the same form as that of the dispensing syringe 4 in Embodiment 1. Namely, the cylinder 40 comprises a large-diameter cylinder body section 40a and a small-diameter dispensing cylinder section 40b molded monolithically with and provided under the large-diameter cylinder body section 40a to form a chip b. The chip b is removably engaged with the nipple-shaped cylindrical assembly section 50 being hanged from a bottom surface of the assembly block 50 provided on the dispensing head a. The small-diameter dispensing cylinder section 40 constituting a lower half portion of the dispensing syringe 4 does not have a tapered portion at the tip, and the end is simply opened as a release port. This release port functions as the dripping port 40c. The piston 41 provided at the lower end portion of the piston rod 41' has a shell-type form tapering downward, and when the piston 41 reaches the dispensing end position at the lower end of the lowering stroke of the piston 41, the tip of the piston 41 is exposed to the outside from a release port at the lower edge of the dispensing cylinder section 40b.

Figure 17:
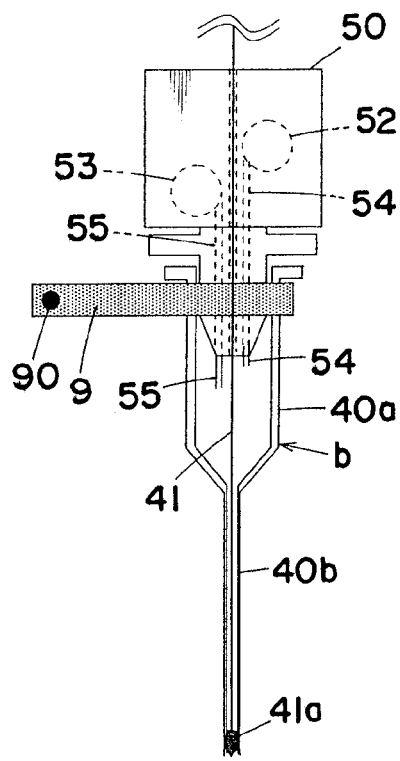
FIG. 17 is a cross-sectional side view illustrating the same above.
Figure 19:
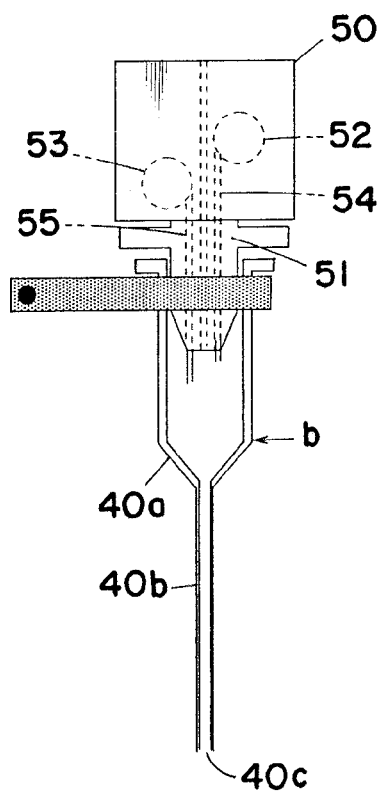
FIG. 19 is a cross-sectional side view illustrating the state in which the assembled chip is held by a holding member in the assembly section in the embodiment shown in FIG. 11.

On the bottom surface of the assembly block 50 which is horizontally long and has a square bar-like form, there are provided a plurality of the nipple-shaped cylindrical assembly sections 51, to each of which the cylinder 40 of the dispensing syringe 4 constituting the chip b is assembled by engaging therein, in parallel to each other in the hanged state. When the cylinders 40 each constituting the chip b are engaged in the cylindrical assembly sections 51 respectively, a plurality of the dispensing syringes 4 are assembled in parallel to each other to the bottom portion of the dispensing head a. For the purpose of stably holding each of the dispensing syringes 4 in the assembled state, there is provided a plate-like holding member 9, which turns upward around a spindle 90 as shown in FIG. 17, at a position slightly away backward from the assembly block 50. The holding member 9 has a notched portion (not shown) capable of engaging with a peripheral surface of the chip b and provided at a position matching, when turned upward, each of the chips b (the cylinder sections of the dispensing syringes 4) provided in parallel to each other. In the state where the chip b has been engaged with and inserted into the cylindrical assembly section 51, when the holding member 9 is turned and the notched portion is engaged with the peripheral surface of the chip, the holding member 9 supports a annular flange provided at an upper edge portion of the chip b as shown in FIG. 19. In this state, when the holding member 9 is hooked with a hooking member (not shown), each of the assembled chips b can be held stably in the assembled state.

Figure 14:
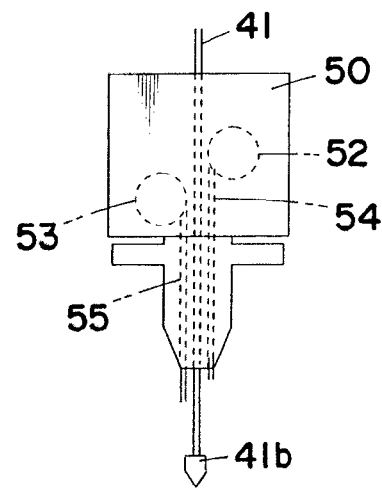
FIG. 14 is a side view illustrating the dispensing syringe assembly section in the embodiment shown in FIG. 11.
Figure 13:
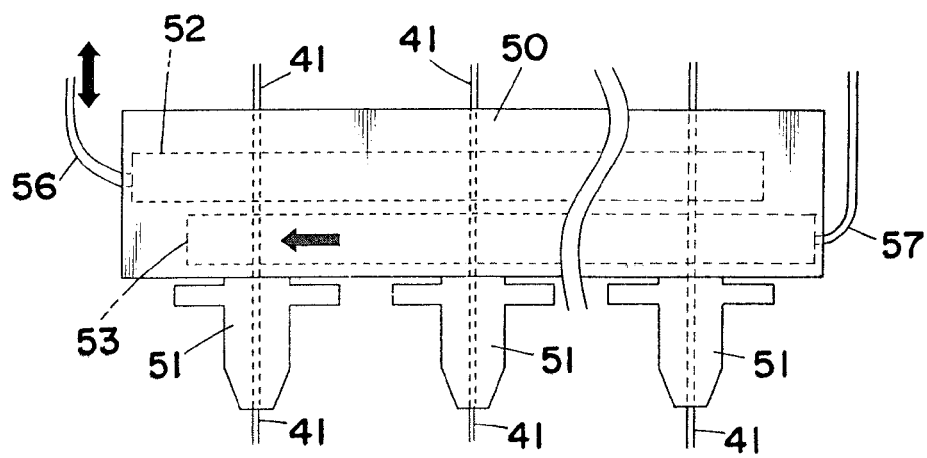
FIG. 13 is a partially omitted front view illustrating a dispensing syringe assembly section in the embodiment shown in FIG. 11.
Figure 15:
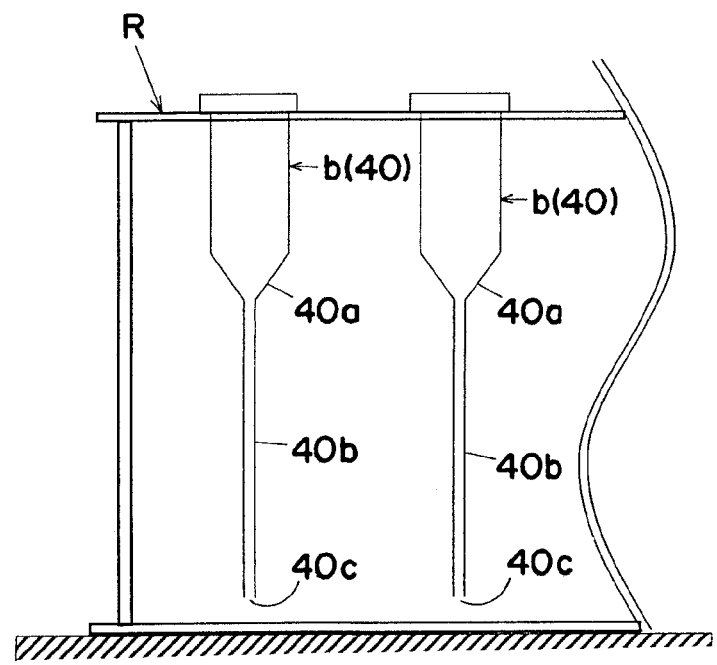
FIG. 15 is a partially omitted front view illustrating a chip rack in the embodiment shown in FIG. 11.
Figure 16:
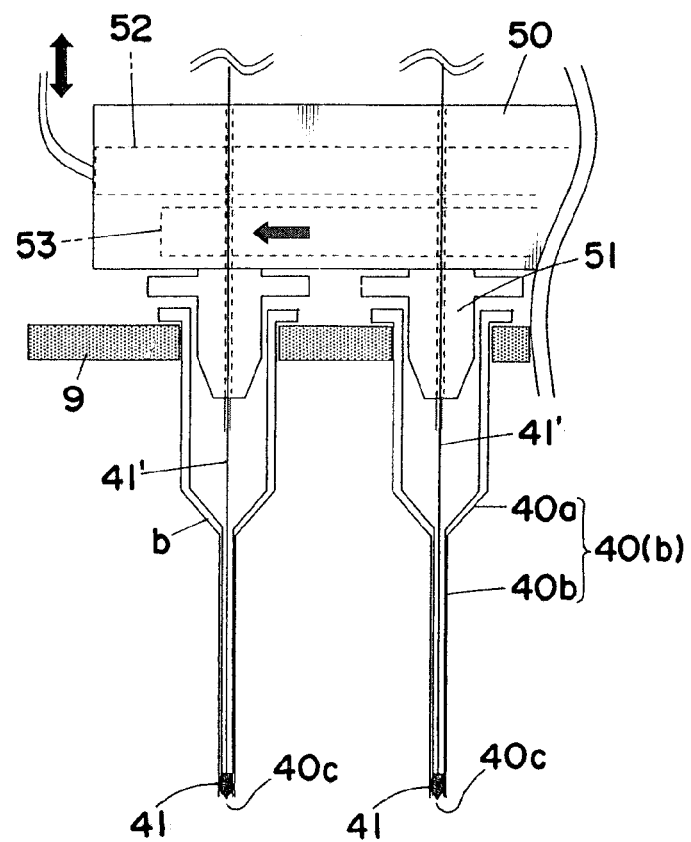
FIG. 16 is a cross-sectional front view illustrating the state where the dispensing syringe has been assembled to the dispensing syringe assembly section in the embodiment shown in FIG. 11.
Figure 18:
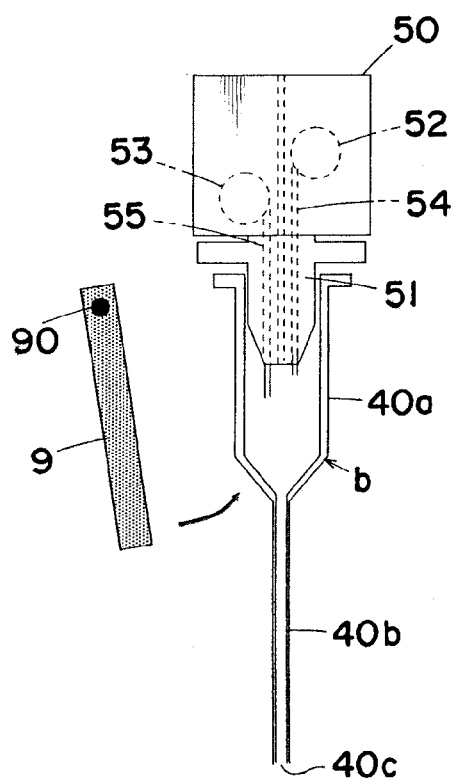
FIG. 18 is a cross-sectional side view illustrating the state where a chip (a dispensing cylinder) has been set on the assembly section in the embodiment shown in FIG. 11.

As shown in FIG. 13, FIG. 14. FIG. 18, and FIG. 19, an air conduit 52 and a liquid conduit 53 each having a form like a shaft hole and extending in the longitudinal direction of the assembly block 50 are provided in the cylindrical assembly section 51 having a square rod-like form with chips b (cylinders 40 of the syringes 4) assembled to a bottom surface thereof. As shown in FIG. 14, an air pipe 54 and a liquid pipe 55 are provided in the path of the conduits 52 and 53 at positions corresponding to the cylindrical assembly portions 51 provided in parallel to each other in the hanged state respectively, and the air pipe 54 and the liquid pipe 55 are connected each as a branch pipe to the conduits 52 and 53 respectively. The air pipe 54 and the liquid pipe 55 are inserted into through-holes provided on the cylindrical assembly section provided in parallel to each other on a bottom surface of the assembly block 50 in the hanged state so that the tip sides of the pipes thrust out from the bottom surface of the assembly block 50. The thrusting portions of the air pipe 54 and the liquid pipe 55 function as nozzles for injecting air and cleaning water to inside of the cylinder body sections 40a of the dispensing syringes 5 assembled to the cylindrical assembly section 51 by engagement and insertion respectively. The air conduit 52 and the liquid conduit 53 provided in the assembly block 50 having a square rod-like shape are sealed at one end thereof, while connection pipes 56 and 57 are connected to the other end thereof. The connection pipes 56 and 57 are alternately communicated to the discharge port of the air-liquid pump sp via a switching valve (not shown).

Because of the configurational features of the dispenser according to the present invention, when the cleaning water injection mechanism 8 is run to clean the inside of the dispensing syringe 4 provided in the dispensing head a, the air-liquid pump sp pumps up cleaning water and sends out the cleaning water from the discharge port. In this step, the discharged cleaning water flows in the liquid conduit 53 and is injected to the inside of each of the cylinder body sections 40a of the syringes 4 assembled in parallel to each other to the assembly section 51. When the cleaning operation with cleaning water is finished and the air-liquid pump pumps out the air, the discharged air flows through the air conduit 52 and is injected to each of the cylinder body sections 40a of the dispensing syringes 4 assembled in parallel to each other to the cylindrical assembly portion 51. Therefore, the dispensing syringes 4 provided in parallel to each other are simultaneously cleaned with the cleaning water.

DESCRIPTION OF SIGNS

G: Liquid surface
H: Air layer
M: Stepping motor
R: Chip rack
R': Holding hole
S: Station
a: Dispensing head
b: Chip
c: Vessel
d: Rack
e: Titration plate
p: Suction pump
p1,p2,p3,p4,p5,p6: Port
sp: Air-liquid pump
t: Cleaning water tank
v: Switching valve
1: Machine (dispenser)
10: Housing
11: Mount
13: Supporting base
14: Chain
15: Sprocket
16: Screw lever
17: Elevating plate
18: Lower supporting base
2: Syringe
20: Cylinder
21: Tip portion a
21: Piston
3: Elevating mechanism
30: Chain belt
31: Sprocket
32: Screw shaft
33: Operating member
4: Dispensing syringe
40: Cylinder
40b: Dispensing cylinder section
40c: Dripping port
41: Piston
41': Piston rod
41a: Sealing section
50: Assembly block
51: Cylindrical assembly section
52: Air conduit
53: Liquid conduit
54: Air pipe
55: Liquid pipe
56, 57: Connection pipe
6: Elevating mechanism
60: Screw shaft
61: Operating member
62: Operating rod
63: Connector
7: Sucking means
70: Suction port
71: Suction cylinder
72: Crank wheel
73: Piston
74: Suction pipe
8: Cleaning water injection means
80: Connection pipe
81: Nozzle
9: Holding member
90: spindle

What is claimed is:
1. A dispenser comprising:
a dispensing head including a cylinder body section having walls defining a cylindrical inner space, a dispensing cylinder section extending downward from the cylinder body section, and having a diameter smaller than that of the inner space of the cylinder body section, and a dripping port at an end of the dispensing cylinder section;
a piston connected to be moved longitudinally through the inner space of the cylinder body section and into the dispensing cylinder section and moving up and down within the dispensing cylinder section, the piston having a diameter sufficiently smaller than a diameter of the inner space of the cylinder body section so as not to come into contact with the walls forming the inner space;
an elevating mechanism connected to the piston to lift and lower the piston between an unsealing position extending out of the dispensing cylinder section and inside the cylinder body section, a dispensing start position located in an upper portion of the dispensing cylinder section and a dispensing end position located in a lower portion of the dispensing cylinder section, wherein a lifting stroke of the piston results in suction of a predetermined quantity of liquid into the dispensing cylinder section through the dripping port, and a lowering stroke of the piston results in dispensing of the liquid sucked into the dispensing cylinder section through the dripping port; and
a sucking mechanism having a suction port connected to extend into and communicate with the cylinder body section to suck air into the cylinder body section and to thereby suck a liquid from the dispensing cylinder section up to a position above the dispensing start position inside the inner space of the cylinder body section when the piston is in said unsealing position extending out of dispensing cylinder section, and wherein the piston is lowered to the dispensing start position under a liquid surface of the liquid within the cylinder body section whenever the dispensing operation is started.
2. The dispenser according to claim 1, wherein the cylinder body section and the dispensing cylinder section are molded into a monolithic unit and the unit is removably assembled to a nozzle section at a bottom surface of the dispensing head.

3. The dispenser according to claim 1, wherein an intermittent control for a lowering operation of the piston can be provided by a driving means.

4. The dispenser according to claim 1, wherein the dispensing head has a cleaning nozzle of a cleaning water injection device capable of injecting cleaning water into the inner space of the cylinder body section.

5. The dispenser according to claim 2, wherein the dispensing head has a cleaning nozzle of a cleaning water injection device capable of injecting cleaning water into the inner space of the cylinder body section.

* * * * *